US00PP36122P2

(12) United States Plant Patent
Weiss

(10) Patent No.: US PP36,122 P2
(45) Date of Patent: Sep. 17, 2024

(54) POINSETTIA PLANT NAMED 'Rockefeller Red'

(50) Latin Name: ***Euphorbia pulcherrima* Wild.**
Varietal Denomination: Rockefeller Red

(71) Applicant: Marcella Weiss, Center Moriches, NY (US)

(72) Inventor: Marcella Weiss, Center Moriches, NY (US)

(73) Assignee: LONG ISLAND BREEDING COMPANY, Center Moriches, NY (US)

( * ) Notice: Subject to any disclaimer, the term of this patent is extended or adjusted under 35 U.S.C. 154(b) by 0 days.

(21) Appl. No.: 18/420,593

(22) Filed: Jan. 23, 2024

(51) Int. Cl.
*A01H 5/02* (2018.01)
*A01H 6/38* (2018.01)

(52) U.S. Cl.
USPC ..... Plt./307
CPC ..... *A01H 6/38* (2018.05)

(58) Field of Classification Search
USPC ..... Plt./307
CPC ..... A01H 6/38; A01H 6/385; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of Poinsettia plant named 'Rockefeller Red', characterized by its upright to slightly outwardly and uniformly mounded plant habit; moderately vigorous to vigorous growth habit; freely and upright to slightly outwardly branching habit; strong and narrowly upright "v-shape" branching habit; dark green-colored leaves; upright to horizontal flower bracts that are bright red in color; prominent, large and dense cyathia clusters; and good post-production longevity.

2 Drawing Sheets

Figure 1:
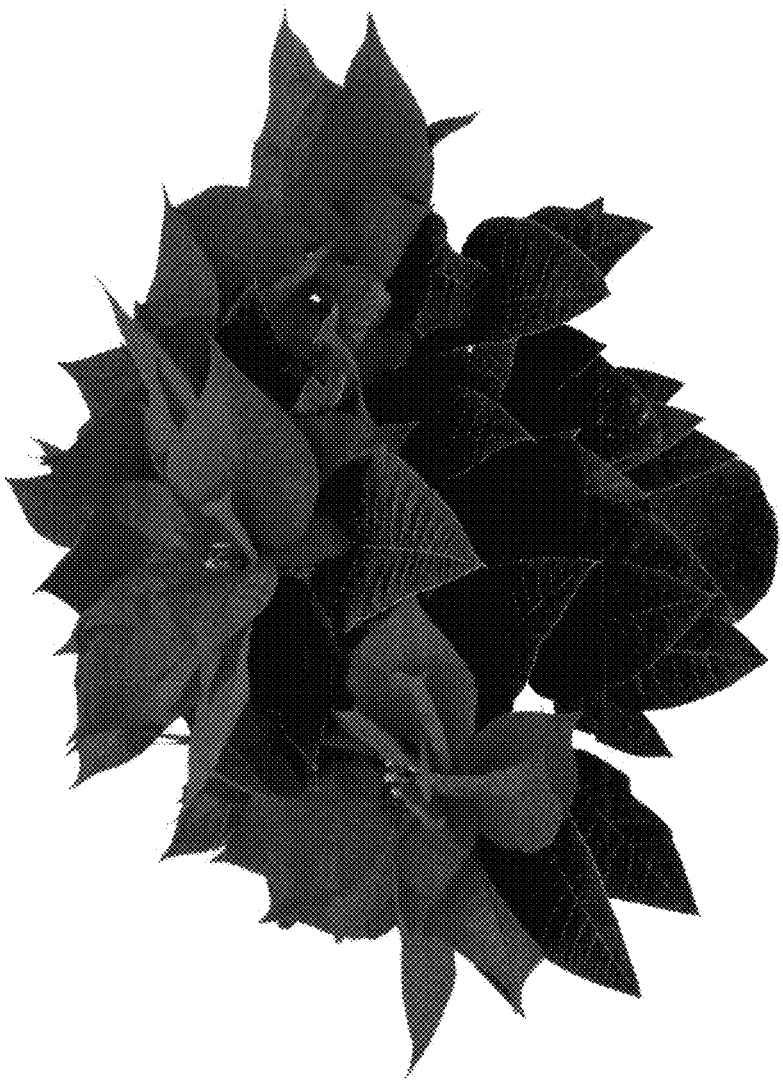

Botanical designation: *Euphorbia pulcherrima* Willd.
Cultivar denomination: 'ROCKEFELLER RED'.

STATEMENT REGARDING PRIOR DISCLOSURES BY INVENTOR/APPLICANT & ASSIGNEE

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of Poinsettia plant, botanically known as *Euphorbia pulcherrima* Willd., and hereinafter referred to by the cultivar name 'Rockefeller Red'.

The new Poinsettia plant is a product of a planned breeding program conducted by the Inventor in Center Moriches, New York. The objective of the breeding program is to create new upright Poinsettia plants with large flower bracts, adaptability to various container sizes and excellent post-production longevity.

The new Poinsettia plant originated from a cross-pollination made by the Inventor in December, 2016 of a proprietary selection of *Euphorbia pulcherrima* Willd. identified as code number EPD5-001, not patented, as the female, or seed, parent, with a proprietary selection of *Euphorbia pulcherrima* Willd. identified as code number EPS2-002, not patented, as the male, or pollen, parent. The new Poinsettia plant was discovered and selected by the Inventor as a single flowering plant from within the progeny of the stated cross-pollination in a controlled greenhouse environment in Center Moriches, New York in November, 2017.

Asexual reproduction of the new Poinsettia plant by terminal vegetative cuttings in a controlled greenhouse environment in Center Moriches, New York since February, 2019 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Rockefeller Red'. These characteristics in combination distinguish 'Rockefeller Red' as a new and distinct Poinsettia plant:

1. Upright to slightly outwardly and uniformly mounded plant habit.
2. Moderately vigorous to vigorous growth habit.
3. Freely and upright to slightly outwardly branching habit; strong and narrowly upright "v-shape" branching habit.
4. Dark green-colored leaves.

5. Upright to horizontal flower bracts that are bright red in color.
6. Prominent, large and dense cyathia clusters.
7. Good post-production longevity.

In side-by-side comparisons, plants of the new Poinsettia differ primarily from plants of the female parent selection in the following characteristics:

1. Plants of the new Poinsettia finish earlier than plants of the female parent selection.
2. Cyathia clusters of plants of the new Poinsettia are larger and more prominent than cyathia clusters of plants of the female parent selection.

In side-by-side comparisons, plants of the new Poinsettia differ primarily from plants of the male parent selection in the following characteristics:

1. Plants of the new Poinsettia have stronger roots than plants of the male parent selection.
2. Plants of the new Poinsettia are more freely branching than plants of the male parent selection.

Plants of the new Poinsettia can be compared to plants of the *Euphorbia pulcherrima* Willd. 'NPCW10158', disclosed in U.S. Plant Pat. No. 22,580. In side-by-side comparisons, plants of the new Poinsettia differ primarily from plants of 'NPCW10158' in the following characteristics:

1. Plants of the new Poinsettia finish earlier than plants of 'NPCW10158'.
2. Plants of the new Poinsettia have larger flower bracts than plants of 'NPCW10158'.
3. Cyathia clusters of plants of the new Poinsettia are larger and more prominent than cyathia clusters of plants of 'NPCW10158'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet (FIG. 1) is a side perspective view of a typical flowering plant of 'Rockefeller Red' grown in a container.

Figure 2:
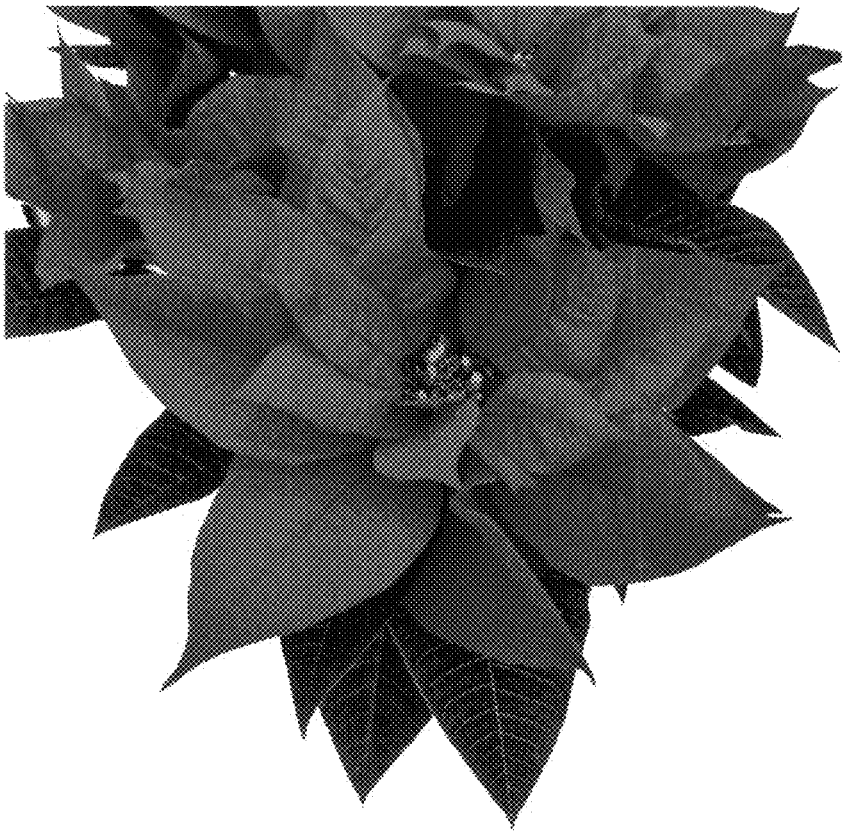

The photograph on the second sheet (FIG. 2) is a close-up view of a typical flowering plant of 'Rockefeller Red'.

DETAILED BOTANICAL DESCRIPTION

Plants used in the aforementioned photographs and in the following detailed description were grown during the summer, autumn and winter in 15.24 cm containers in glass and polyethylene-covered greenhouses in Center Moriches, New York under natural season conditions and cultural practices typical of commercial Poinsettia production. During the production of the plants, day temperatures ranged from 21 ° C. to 32° C. and night temperatures ranged from 18° C. to 23° C. Plants were pinched one time and were six months from unrooted cuttings when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. 'Rockefeller Red'.

Parentage:

*Female, or seed, parent*.—Proprietary selection of *Euphorbia pulcherrima* Willd. identified as code number EPD5-001, not patented.

*Male, or pollen, parent*.—Proprietary selection of *Euphorbia pulcherrima* Willd. identified as code number EPS2-002, not patented.

Propagation:

*Type*.—Terminal vegetative cuttings.

*Time to initiate roots, summer*.—About 10 to 14 days at ambient daytime temperatures about 27° C. to 29° C.; ambient nighttime temperatures about 21° C. to 24° C.; and soil temperatures about 20° C. to 22° C.

*Time to initiate roots, winter*.—About 10 to 14 days at ambient daytime temperatures about 21° C. to 22° C.; ambient nighttime temperatures about 20° C. to 24° C.; and soil temperatures about 20° C. to 21° C.

*Time to produce a rooted young plant, summer*.—About 28 to 35days at ambient daytime temperatures about 27° C. to 29° C.; ambient nighttime temperatures about 21° C. to 24° C.; and soil temperatures about 20° C. to 21° C.

*Time to produce a rooted young plant, winter*.—About 35 to 40days at ambient daytime temperatures about 21° C. to 22° C.; ambient nighttime temperatures about 20° C. to 21° C.; and soil temperatures about 20° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to slightly outwardly spreading and uniformly mounded plant habit; broad inverted triangle; inflorescences with numerous flower bracts positioned above the foliar plane; moderately vigorous to vigorous growth habit and moderate growth rate.

*Plant height*.—About 32 cm to 35 cm.

*Plant diameter or spread*.—About 38 cm to 42 cm.

*Lateral branch description*.—Branching habit: Freely branching habit, about eight to ten lateral branches develop after pinching; upright to slightly outwardly branching habit; strong and narrowly upright "v-shaped" branching habit. Length: About 18 cm to 20 cm. Diameter: About 6 mm to 7 mm. Internode length: About 1.2 cm to 1.5 cm. Strength: Strong. Aspect: About 30° to 35° from vertical. Texture and luster: Smooth, glabrous; glossy. Color: Close to between 146A and 147A.

*Leaf description*.—Arrangement: Alternate, simple. Length: About 10 cm to 12 cm. Width: About 7 cm to 7.5 cm. Shape: Ovate, not lobed. Apex: Acuminate. Base: Truncate with cordate or hastate tendencies. Margin: Entire; slightly undulate. Aspect: Mostly upright to horizontal and eventually slightly downward with subsequent development. Texture and luster, upper surface: Smooth, glabrous; velvety; slightly glossy. Texture and luster, lower surface: Prominent venation, glabrous; slightly glossy. Venation pattern: Pinnate, arcuate. Color: Developing leaves, upper surface: Darker green than 147A to close to between 147A and N189A. Developing leaves, lower surface: Close to 146A. Fully expanded leaves, upper surface: Close to N189A to darker green than N189A; midvein, close to 146A variable overlain with close to 59A, and lateral venation, indistinguishable from lamina color. Fully expanded leaves, lower surface: Close to 147A; midvein, close to 146A variably overlain with close to 59A, and lateral venation, indistinguishable from lamina color. Leaf petioles: Length: About 4.5 cm to 5 cm. Diameter: About 3 mm. Texture and luster, upper and lower surfaces: Smooth, glabrous; glossy. Color, upper and lower surfaces: Close to 59A.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower about eight weeks after planting rooted cuttings in Center Moriches, New York.

*Post-production longevity*.—Good post-production longevity; plants of the new Poinsettia maintain good substance and flower bract color for about five to six weeks under interior conditions, temperature-dependent; flower bracts persistent and cyathia not persistent.

*Inflorescence diameter*.—About 20 cm to 22 cm.

*Inflorescence height* (*depth*).—About 8 cm.

*Flower bracts*.—Quantity per inflorescence: About 22 to 25. Length, largest bracts: About 11 cm to 12 cm. Width, largest bracts: About 6.75 cm to 7.75 cm. Shape: Ovate, not lobed. Apex: Acuminate. Base: Truncate or attenuate. Margin: Entire; slightly undulate. Aspect: Upright to about 60° from vertical. Texture and luster, upper surface: Slightly rugose, glabrous; velvety; slightly glossy. Texture and luster, lower surface: Rugose with prominent venation, glabrous; somewhat velvety; matte. Venation pattern: Pinnate, arcuate. Color: Developing and fully developed bracts, upper surface: Close to N45A; midvein, close to N45A variably overlain with close to 59A to 59B, lateral venation, indistinguishable from lamina color; color does not change with subsequent development. Developing and fully developed bracts, lower surface: Close to N45C to N45D; midvein, close to N45C to N45D variably overlain with close to 59A, lateral venation, indistinguishable from lamina color; color does not change with subsequent development. Bract petioles: Length: About 2 cm to 2.5 cm. Diameter: About 2.25 mm by 2.5 mm. Texture and luster, upper and lower surfaces: Smooth, glabrous; glossy. Color, upper and lower surfaces: Close to 59A.

*Cyathia*.—Quantity per corymb: About 12 to 15; relatively large, dense and prominent. Length: About 9 mm to 11 mm. Width: About 5 mm to 6 mm. Shape: Narrowly ovoid. Texture and luster: Smooth, glabrous; slightly glossy. Color, immature: Close to 144A. Color, mature: Close to 146A.

*Nectaries*.—Quantity per cyathium: Typically one. Length: About 7.5 mm to 8 mm. Width: About 4 mm. Shape: Elliptic. Texture and luster: Smooth, glabrous; slightly glossy. Color, inner and outer surfaces: Close to 9A and 13A.

*Peduncles*.—Length: About 2.5 mm. Diameter: About 1.5 mm. Strength: Strong. Aspect: Mostly upright to slightly outwardly. Texture and luster: Smooth, glabrous; slightly glossy. Color: Close to 146A.

*Reproductive organs*.—Stamens: Quantity per cyathium: About eight to twelve. Filament length: About 4 mm. Filament color: Close to 59A. Anther shape: Round to oval; bi-lobed. Anther length: Less than 1 mm. Anther color: Close to 59A. Amount of pollen: None observed. Pistils: Quantity per cyathium: If present, one; tri-parted. Pistil length: About 5 mm. Style length: About 4 mm. Style color: Close to 59A. Stigma shape: Three-parted, recurved. Stigma color: Close to 59A. Ovary color: Close to 144C to 144D.

*Seeds and fruits*.—To date, seed and fruit production have not been observed on plants of the new Poinsettia.

Pathogen & pest resistance: To date, plants of the new Poinsettia have not been observed to be resistant to pathogens and pests common to Poinsettia plants.

It is claimed:

1. A new and distinct Poinsettia plant named 'Rockefeller Red' as illustrated and described.

* * * * *